(12) United States Patent
McGrath et al.

(10) Patent No.: US 8,845,525 B2
(45) Date of Patent: Sep. 30, 2014

(54) LARYNGOSCOPE INSERTION SECTION WITH TUBE GUIDE FOR GUIDING ENDOTRACHEAL TUBES HAVING A RANGE OF EXTERNAL DIAMETERS

(75) Inventors: Matthew John Ross McGrath, Edinburgh (GB); Peter Douglas Colin Inglis, Edinburgh (GB)

(73) Assignee: Aircraft Medical Limited, Edinburgh (GB)

( * ) Notice: Subject to any disclaimer, the term of this patent is extended or adjusted under 35 U.S.C. 154(b) by 182 days.

(21) Appl. No.: 13/254,582

(22) PCT Filed: Mar. 3, 2010

(86) PCT No.: PCT/GB2010/050376
§ 371 (c)(1),
(2), (4) Date: Nov. 10, 2011

(87) PCT Pub. No.: WO2010/100495
PCT Pub. Date: Sep. 10, 2010

(65) Prior Publication Data
US 2012/0095295 A1    Apr. 19, 2012

(30) Foreign Application Priority Data
Mar. 3, 2009    (GB) .................................. 0903611.2

(51) Int. Cl.
*A61B 1/267* (2006.01)
*A61M 16/04* (2006.01)
(52) U.S. Cl.
CPC ............ *A61B 1/267* (2013.01); *A61M 16/0488* (2013.01)
USPC ............................ 600/194; 600/193; 600/196

(58) Field of Classification Search
USPC ......................................... 600/193, 194, 196
See application file for complete search history.

(56) References Cited

U.S. PATENT DOCUMENTS

| | | | |
|---|---|---|---|
| 5,651,761 A | 7/1997 | Upsher | |
| 5,682,880 A | 11/1997 | Brain | |
| 5,840,013 A | 11/1998 | Lee et al. | |
| 7,946,981 B1 * | 5/2011 | Cubb | ............................ 600/194 |
| 2002/0117171 A1 | 8/2002 | Parker | |
| 2004/0240081 A1 | 12/2004 | Saito | |
| 2005/0090712 A1 | 4/2005 | Cubb | |
| 2005/0240081 A1 | 10/2005 | Eliachar | |
| 2008/0216827 A1 | 9/2008 | Seydel et al. | |

FOREIGN PATENT DOCUMENTS

WO       WO 83/01373       4/1983

OTHER PUBLICATIONS

International Search Report for PCT/GB2010/050376, mailed Jun. 9, 2010.

* cited by examiner

*Primary Examiner* — Andrew Yang
(74) *Attorney, Agent, or Firm* — Nixon & Vanderhye P.C.

(57) ABSTRACT

A laryngoscope insertion section includes an elongate support member and a tube guide having a resilient tube guiding member, to enable the insertion section to be used with endotracheal tubes having a wide range of external diameters. The breadth and/or thickness of the insertion section can therefore be less when retaining an endotracheal tube having a relatively small external diameter, enabling the insertion section to reliably guide tubes having a range of external diameters and to reliably guide relatively small external diameter tubes while occupying less volume that would otherwise be required in order for the tube guide to be able to guide tubes having a larger external diameter.

14 Claims, 3 Drawing Sheets

LARYNGOSCOPE INSERTION SECTION WITH TUBE GUIDE FOR GUIDING ENDOTRACHEAL TUBES HAVING A RANGE OF EXTERNAL DIAMETERS

This application is the U.S. national phase of International Application No. PCT/GB2010/050376 filed 3 Mar. 2010 which designated the U.S. and claims priority to GB Patent Application No. 0903611.2 filed 3 Mar. 2009, the entire contents of each of which are hereby incorporated by reference.

FIELD OF THE INVENTION

The present invention relates to the field of laryngoscope insertion sections having tube guides for detachably retaining and guiding endotracheal tubes during intubation. Insertion sections according to the invention are suitable for guiding endotracheal tubes having a range of external diameters.

BACKGROUND TO THE INVENTION

Laryngoscopes are medical devices which are employed to introduce endotracheal tubes into patient's airways, for example, when a patient is being anaesthetised. Laryngoscopes comprise insertion sections, which are the part of a laryngoscope which extends towards and into a patient's oral cavity during intubation. Insertion sections may be removably attachable to a laryngoscope body, integral parts of laryngoscopes or themselves function as laryngoscopes. As well as an insertion section, laryngoscopes typically comprises a handle which is usually elongate and which may be arranged at an angle to the proximal end of the insertion section or generally parallel to the proximal end of the insertion section, or at any angle therebetween. Laryngoscopes further include a source of light and a number of known devices, referred to as video laryngoscopes, include imaging devices, for example integral video cameras or fibre-optic bundles for attachment to external video cameras, to enable a user to view the distal tip of an endotracheal tube as it is being introduced into a patient's larynx.

Traditional laryngoscope insertion sections, such as insertion sections known in the art as Miller, Macintosh or Wisconsin blades, function to lift a patient's tissue adjacent the epiglottis to enable a tube to be inserted into a patient's larynx and to enable the patient's larynx to be viewed during intubation. However, they do not guide tubes as such.

A number of designs are known which do include a tube guide. For example, WO 04/073510 (Gandarias) discloses a laryngoscope having a lateral tube guide extending along the majority of the length of the insertion section. A tube guide enables an endotracheal tube to be detachably retained by the insertion section while it is introduced into a patient's larynx. In principle, the provision of a tube guide may facilitate intubation by introducing the endotracheal tube into the oral cavity at the same time as the insertion section and by directing a tube towards the larynx. However, tube guides increase the overall bulk of insertion sections and it is desirable to provide a tube guide which adds as little bulk as possible to the insertion section.

Endotracheal tubes come in a wide range of external diameters, for use with patients of different dimensions. Laryngoscope insertion sections with tube guides are typically only suitable for intubating using endotracheal tubes having a relatively narrow range of external diameters. Thus, insertion sections must typically be provided with tube guides in a range of sizes. Not only does this increase manufacturing costs and require users to stock several types of insertion section, there is a risk that the wrong sized insertion section might be selected during intubation, or that a user may not have the correct size of insertion section for use with an endotracheal tube having a particular external dimension appropriate to the patients who is to be intubated.

In order to enable an insertion section to be used with insertion sections of a wide range of external diameters, a tube guide may be provided which is of fixed relatively broad cross-section, such as to be able to retain endotracheal tubes of up to a predetermined maximum external diameter. However, any such tube guide is unlikely to adequately guide tubes having a relatively small external diameter.

Furthermore, any such tube guide will be bulkier than is necessary when retaining and guiding endotracheal tubes of relatively small external diameter.

Accordingly, the invention aims to provide a laryngoscope insertion section with a tube guide which reliably guides endotracheal tubes of a relatively wide range of external diameters. Some embodiments of the invention aim to provide a laryngoscope insertion section which is usable to reliably guide endotracheal tubes of a wide range of external diameters without being excessively bulky when guiding endotracheal tubes with external diameters at the lower end of an operating range of endotracheal tube size.

SUMMARY OF THE INVENTION

According to a first aspect of the present invention there is provided a laryngoscope insertion section having a proximal end and a distal end for insertion into a patient's oral cavity, the insertion section comprising a tube guide for retaining an endotracheal tube and guiding a retained endotracheal tube towards a patient's larynx, the tube guide comprising a resilient tube guiding member biased towards a first position for retaining endotracheal tubes of a first external diameter and operable to a second position for retaining endotracheal tubes of a second external diameter, which second external diameter is greater than the first external diameter, by the insertion of an endotracheal tube of the second external diameter.

Thus, the resilient tube guiding member is moveable, against biasing arising from the resilient nature of the tube guiding member, from the first position to the second position to retain endotracheal tubes of the second external diameter but can remain in the first position to retain endotracheal tubes of the first external diameter. This can increase the range of external diameters of endotracheal tubes which can be reliably guided by the insertion section. Preferably, the second external diameter is at least 110%, at least 125% and more preferably at least 150% of the first external diameter. Preferably, the said first external diameter is the diameter of the smallest external diameter endotracheal tube in an operating range of external tube diameters and the said second external diameter is the diameter of the largest external diameter endotracheal tube in an operating range of external tube diameters.

Typically, the tube guide comprises a central axis and the second position is further from the central axis than the first position. Preferably, the thickness and/or breadth of the insertion section in a cross-section through the resilient tube guiding member is less when the resilient tube guiding member is in the first position than the second position. Thus, the overall thickness and/or breadth of the insertion section is less at the location of the resilient tube guiding member when retaining small external diameter endotracheal tubes but remains able to retain and guide larger external diameter endotracheal tubes. By a central axis we refer to a virtual line extending along the middle of the insertion section from the proximal end of the insertion section to the distal end of the insertion section and do not intend to imply any symmetry.

Within this specification and the appended claims, the inferior surface is the surface of an insertion section which faces the patient's tongue in use. The opposite surface is referred to as the superior surface. Words such as inferior, inferiorly, superior and superiorly are used in corresponding senses. A superior-inferior axis is a virtual axis extending parallel to the superior and inferior directions.

By the thickness of an insertion section, we refer to the displacement, parallel to a superior-inferior axis, from the most inferior point on the inferior side of the insertion section to the most superior point on the superior side of the insertion section, through a given cross-section orthogonal to the length of the insertion section. Words such as "thick", "thicker", "narrow", and "narrower" should be construed accordingly.

By the breadth of an insertion section, we refer to the displacement in a lateral direction, orthogonal to the superior-inferior axis, from the point furthest displaced from a central axis of the insertion section orthogonal to the superior-inferior axis, in one sense, to the point furthest displaced from a central axis of the insertion section orthogonal to the superior-inferior axis, in the opposite sense.

Typically, the insertion section comprises an elongate support member. The elongate support member may be adapted to support an image collector in use or to receive an image collector support in use. The elongate support member may comprise an elongate channel for receiving an image collector and image collector support in use.

Typically the tube guide is arranged to guide an endotracheal tube along a transverse side of the elongate support member, for example the inferior side, the superior side, or a lateral side of the elongate support member. The tube guide may comprise one or more tube guiding members extending transversely (e.g. inferiorly, superiorly or laterally) from the elongate support member, one of which may be the resilient tube guiding member.

Preferably, the tube guide is located on a lateral side of the elongate support member. Preferably, the tube guide is arranged to retain an endotracheal tube along a lateral side of the insertion section such that is does not extend entirely inferiorly or entirely superior of the adjacent elongate support member between the most proximal and most distal locations where a retained endotracheal tube contacts the insertion section. In this case, the overall thickness and/or breadth of the insertion section, or both, at the resilient tube guiding member may be greater when the resilient tube guiding member is in the second position than in the first position.

The tube guide may be arranged to retain an endotracheal tube along the inferior side, or the superior side, of the insertion section in which case the resilient tube guiding member is preferably operable to move in the inferior direction, or superior direction, respectively between the first position and the second position. In this case, the overall thickness and/or breadth of the insertion section at the resilient tube guiding member is typically greater when the resilient tube guiding member is in the second position than in the first position.

Thus, a tube guide having a thickness and/or breadth which varies depending on the external diameter of a received endotracheal tube may be provided, even where the thickness of an adjacent elongate support member is fixed, for example, because the elongate support member must have defined dimensions to receive an image collector support and/or to detachably connect the insertion section to an insertion section retaining formation of a laryngoscope. In this, case the overall breadth of the insertion section is typically greater when the resilient tube guiding member is in the second position than in the first position.

The resilient tube guiding member may comprise or consist of resilient material. The resilient tube guiding member may comprise a rigid tube guiding portion and a resilient connector, such as a resilient hinge, through which the rigid tube guiding portion is attached to the elongate support member, adjacent the resilient tube guiding member.

The resilient tube guiding member may extend along a relatively small proportion of the length of the insertion section, for example, less than 10% of the length of the insertion section. However, it may be that the resilient tube guiding member extends along the majority of the length of the insertion section. The resilient tube guiding member may extend from the most proximal location where the endotracheal tube is guided by the tube guide to the most distal location where the endotracheal tube is guided. Thus, the tube guide may comprise an elongate channel having opposed walls, one wall of which functions as the resilient tube guiding member.

The resilient tube guiding member may function as a deformable sleeve. The resilient tube guiding member may conform to the shape of a retained endotracheal tube.

A plurality of said resilient tube guiding members may be provided.

Within this specification and the appended claims, by the external diameter of the largest external diameter endotracheal tube in an operating range of endotracheal tube sizes, we refer to the external diameter of the largest external diameter endotracheal tubes with which the insertion section can be reliably used. This will depend on the scale of the insertion section which will itself depend on the application of the insertion section. An insertion section for use with adult humans may, for example, be adapted to be usable reliably with endotracheal tubes with an external diameter of up to 12.3 mm. Tubes of this external diameter are referred to as Size 9.0 in the field. The minimum external diameter may be around 5.5 mm. Where the insertion section is made from a plastics material, the mean thickness of the inferior and first superior tube guiding members typically requires to be at least 0.75 mm (preferably around 1.5 mm) to provide suitable mechanical strength for internal use. Accordingly, the thickness of the first region is preferably less than 15.3 mm, more preferably less than 14.6 mm, 13.8 mm or more preferably less than 13.1 mm, in the case of an insertion section for inserting endotracheal tubes into adult humans.

The dimensions of an insertion section for use with infant humans, including new born infants, are typically scaled proportionately from the dimensions of an insertion section for use with human adults. Nevertheless, the proportions of some features, such as the thickness of the tube guiding members, may not scale proportionately. In the case of an insertion section for inserting endotracheal tubes into infant humans, including new born infants, the operating range of external tube diameters may be 1.0 to 5.0 mm, and the thickness of the first region is preferably less than 8.0 mm, preferably less than 7.0 mm, or more preferably less than 6.0 mm.

Preferably, the tube guide is a tube guide for removably retaining an endotracheal tube.

The or each resilient tube guiding member may be formed from two material of different resilience. This can facilitate the concurrent provision of sufficient structural integrity to retain a tube and sufficient flexibility to accommodate larger diameter tubes and to enable tubes to be removable from the tube guide. This can be achieved, for example, using a twin skin injection moulding procedure. The or each resilient tube guiding member may taper at a proximal and/or distal end, to achieve the same effect of the tapered regions having different structural properties as a result of their lower bulk.

When the or each resilient tube guiding member is in the first position it may be well suited to retain a bougie, or other introducer, or a fibre optic cable, for example of a diameter of 4-6 mm in an insertion section for intubating adult humans.

According to a second aspect of the present invention there is provided a laryngoscope insertion section having a proximal end and a distal end for insertion into a patient's oral cavity, the insertion section comprising a tube guide for retaining an endotracheal tube and guiding a retained endotracheal tube towards a patient's larynx, wherein the thickness and/or the breadth of the tube guide is variable at at least one intraoral region located so as to be within a patient's oral cavity when the insertion section is fully inserted into a patient's oral cavity, to enable the overall thickness and/or breadth respectively of the insertion section at the intraoral region to vary depending on the external diameter of an endotracheal tube retained by the tube guide.

Thus, the thickness and/or breadth of the insertion section, at the intraoral region, may be larger when an endotracheal tube having the largest external diameter in an operating range of endotracheal tube sizes is retained by the tube guide than when an endotracheal tube having the lowest external diameter in an operating range of endotracheal tube sizes is retained by the tube guide.

Typically, the insertion section comprises an elongate support member. The elongate support member may be adapted to support an image collector in use or to receive an image collector support in use. The elongate support member may comprise an elongate channel having an opening at its proximal end for receiving an image collector and image collector support in use.

Preferably, the insertion section comprises a said elongate support member and one or more tube guiding members which extends from the elongate support member, wherein a tube guiding member is resiliently mounted to the elongate support member at the intraoral region such as to vary the overall thickness or breadth of the insertion section dependent on the external diameter of a retained endotracheal tube. Thus, the tube guiding member may be a resilient tube guiding member.

The resilient tube guiding member may comprise or consist of resilient material. The resilient tube guiding member may comprise a rigid tube guiding portion and a resilient connector, such as a resilient hinge, through which the rigid tube guiding portion is attached to the elongate support member, adjacent the resilient tube guiding member.

The tube guide may be located on the inferior or superior side of the elongate support member, in which case the said tube guiding member is typically located on the inferior or superior side respectively of the elongate support member.

Preferably, the tube guide is located on a lateral side of the elongate support member. Preferably, the tube guide is arranged to retain an endotracheal tube along a lateral side of the insertion section such that it does not extend entirely inferiorly or entirely superior of the adjacent elongate support member between the most proximal and most distal locations where a retained endotracheal tube contacts the insertion section.

Preferably, the insertion section extends distally of the moveable tube guiding member. Thus, a given deformation of the said tube guiding member will typically have a greater effect on the position of the distal end of a retained endotracheal tube extending beyond the distal end of the insertion section and adjacent to a patient's larynx in use than would be the case if the said tube guiding member was located at the distal end of the insertion section.

The insertion section may be integral to a laryngoscope. The insertion section may be demountably attachable to a laryngoscope. Preferably, the insertion section comprises an elongate cavity extending along part of the length of the insertion section to enable the insertion section to be demountably attached to an insertion section retaining member of a laryngoscope.

Preferably, the tube guide is a tube guide for removably retaining an endotracheal tube.

According to a third aspect of the invention there is provided a laryngoscope having an insertion section retaining formation to demountably retain an insertion section according to the first or second aspect of the invention. The invention also extends to a laryngoscope comprising a handle and an insertion section according to the first or second aspect of the invention fixedly attached thereto.

The laryngoscope preferably comprises a light source. The elongate cavity may be operable to encompass the light source in use and the insertion section may comprise a translucent or transparent portion to enable light from the light source to be shone on a patient's larynx in use. Thus, the insertion section may function to protect the light source from contact with bodily fluids and/or air during use.

The light source may be a light generating device, for example a light emitting diode or a bulb. The light source may be a light emitting region of a light conduit operably connected to or connectable to a light generating device.

The laryngoscope preferably comprises an image collector. The elongate cavity may be adapted to encompass an image collector in use. The image collector may be a camera. The image collector may comprise a light collecting region of a light conduit and the light conduit may be operable to conduct light to a camera.

The insertion section retaining formation may comprise an elongate image collector support including the image collector and arranged to extend into the elongate cavity in use so as to collect images of a region including a patient's larynx during intubation.

The elongate image collector support may comprise a rigid strengthening element. For example, it may comprise an elongate rigid metal housing. The light source may also be mounted in or on the elongate image collector. However, the elongate image collector support may be flexible.

In embodiments including an image collector for imaging the larynx during intubation, and at least one manual control for controlling movement of the moveable tube guiding member, the image collector, the insertion section, at least one manual control and the moveable tube guiding member may be formed and arranged (e.g. configured) so that movement of a said at least one manual control moves the tip of a retained endotracheal tube vertically up or down in the images collected by the image collector. The image collector, the insertion section, a second manual control and the moveable tube guiding member may be formed and arranged (e.g. configured) so that movement of the second manual control moves the tip of a retained endotracheal tube left or right in the images collected by the image collector. This facilitates easy adjustment of the location of a retained endotracheal tube relative to a patient's larynx during intubation.

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
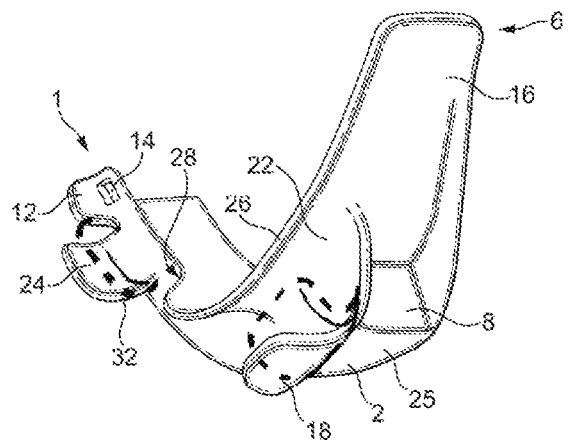
FIGS. 1 to 3 are perspective views from a range of orientations of an alternative laryngoscope insertion section.
Figure 2:
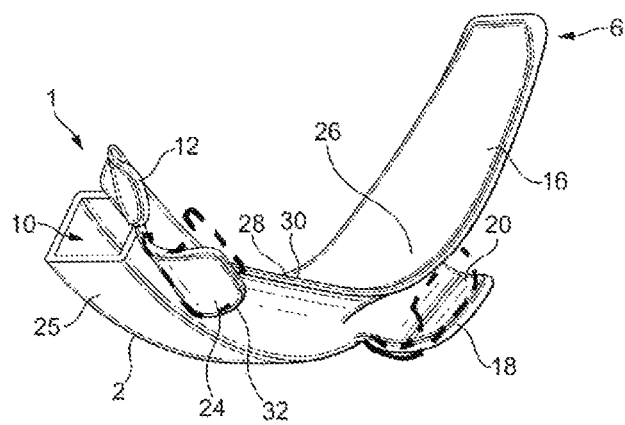
Figure 3:
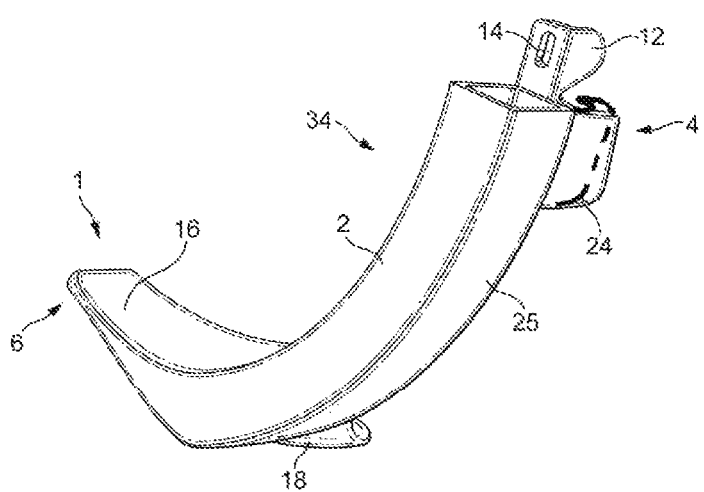

With reference to FIGS. 1 to 3, a laryngoscope insertion section for use with adult humans, shown generally as 1, comprises an elongate support member 2 which extends from the proximal end of the insertion section 4 but does not extend as far as the distal end of the insertion section 6. The elongate support member has a light-permeable viewing port 8 at its distal end. An elongate bore 10 extends along the elongate support member from the proximal end of the elongate support member for receiving and retaining an insertion section retaining protrusion of a laryngoscope and covering the insertion section retaining protrusion to protect it from bodily fluids in use. A retaining portion 12, which includes a fixing aperture 14 for engaging with a corresponding protrusion on an insertion section supporting member of a laryngoscope, facilitates the removable attachment of the insertion section to a laryngoscope. The insertion section may be used with a laryngoscope including a insertion section retaining member with a video camera and light source which is included in the insertion section retaining member, so that light from the light source can illuminate a patient's larynx and the surrounding region and the video camera can relay images of the patient's larynx and the surrounding region to a display. A broad protrusion 16 extends from the end of the elongate support member, which functions as a blade for contacting and typically lifting a patient's anatomy in use to provide clear access to the larynx.

A tube guide extends laterally of the elongate support member. The tube guide comprises a distal superior tube guiding member 18, located towards the distal end of the insertion section, which extends from the superior side of the elongate support member and functions as the first superior tube guiding member. The proximal and distal superior tube guiding members are resilient, as discussed further below. The proximal and distal superior tube guiding members are shown in the configuration they adopt while retaining an endotracheal tube at the upper end of an operating range of endotracheal tube sizes and the dashed lines show the proximal and distal superior tube guiding members in the configuration which they adopt when no endotracheal tube is retained. The inferior surface of the distal superior tube guiding member includes a tube guiding surface 20 which is arranged to contact and thereby guide the superior surface of a retained endotracheal tube. A lateral edge 22 of the elongate support member does not function as the tube guiding surface as, although it may contact an endotracheal tube in use, it does not contact and thereby guide the superior surface of a retained endotracheal tube.

The tube guide also comprises a proximal superior tube guiding member 24, located towards the proximal end of the insertion section, which extends laterally from the elongate support member and functions as the second superior tube guiding member. The inferior surface of the proximal superior tube guiding member also includes a tube guiding surface which is arranged to contact and thereby guide the superior surface of a retained endotracheal tube.

The tube guiding surfaces of the proximal and distal superior tube guiding members are generally incurvate. The proximal and superior tube guiding members are of generally even thickness and extend laterally and superiorly from the elongate support member, from a location on the lateral side of the elongate support member which is near to but not level with the superior surface 25 of the elongate support member. They extend superiorly to the superior surface of the elongate support member, curve over a retained endotracheal tube in use and then curve laterally and inferiorly to extend over and guide the superior surface of a retained endotracheal tube. The tube guiding surface of the proximal superior tube guiding member extends superiorly relative to the insertion section towards its distal end. The tube guiding surface of the distal superior tube guiding member extends inferiorly relative to the insertion section towards its distal end. This arrangement facilitates the retention of an endotracheal tube with a greater curvature than the insertion section.

An inferior tube guiding member 26 extends from a location which is distal of the proximal superior tube guiding member towards the distal end of the insertion section. The inferior tube guiding member comprises a tube guiding surface which is arranged to contact and thereby guide the inferior surface of a retained endotracheal tube. The inferior tube guiding member tapers at a proximal end and so it also comprises an inferior surface portion 28 which does not function as a tube guiding surface because it does not contact and thereby guide the inferior surface of a retained endotracheal tube in use.

The tube guiding surfaces of the inferior tube guiding member is also generally incurvate. The inferior tube guiding member is of generally even thickness and extends laterally and inferiorly from the elongate support member, from a location on the lateral edge of the elongate support member which is near to but not level with the inferior surface 25 of the elongate support member. The inferior tube guiding member extends inferiorly to the inferior surface of the elongate support member, curves over a retained endotracheal tube in use and then curves laterally and superiorly to extend under and guide the inferior surface of a retained endotracheal tube.

The tube guide is arranged to leave the inferior and superior surfaces of a retained endotracheal tube exposed along a majority of the length of the insertion section between the most proximal and most distal locations where the endotracheal tube contacts a retained endotracheal tube. In an insertion section for use with adult humans, the length of the proximal superior tube guiding member, along its most superior region, may be approximately 22 mm and the length of the distal superior tube guiding member, along its most superior region, may be approximately 15 mm. The distance between the distal end of the proximal superior tube guiding member and the proximal end of the distal superior tube guiding member, following the curve of the insertion section, between the most superior regions of the proximal and distal superior tube guiding members, may be approximately 68 mm, or 65 mm in a direct line. The distance between the proximal end of the inferior tube guiding member and the distal end of the proximal superior tube guiding member may be approximately 25 mm and the inferior tube guiding member may extend approximately 45 mm proximally of the proximal end of the distal superior tube guiding member.

The inferior tube guiding member and the distal superior tube guiding member are arranged to guide a retained endotracheal tube 29 towards a patients' larynx in use. The tube guiding surfaces of the proximal and distal superior tube guiding members are spaced apart because the proximal and distal superior tube guiding members are spaced apart. The superior surface of a retained endotracheal tube is exposed between the tube guiding surfaces of the proximal and distal superior tube guiding members. The inferior tube guiding member extends proximally of the distal superior tube guiding member and so there is a region where a retained endotracheal tube is guided on its inferior side but not its superior side. The proximal end 30 of the tube guiding surface inferior tube guiding member is spaced apart from the distal end 32 of the proximal superior tube guiding member, by a sufficient distance to enable a 12.3 mm external diameter endotracheal tube (being the upper end of an operating range of endotracheal tube sizes) to be introduced at an angle to the centre line of the insertion section.

Figures 4, 6:
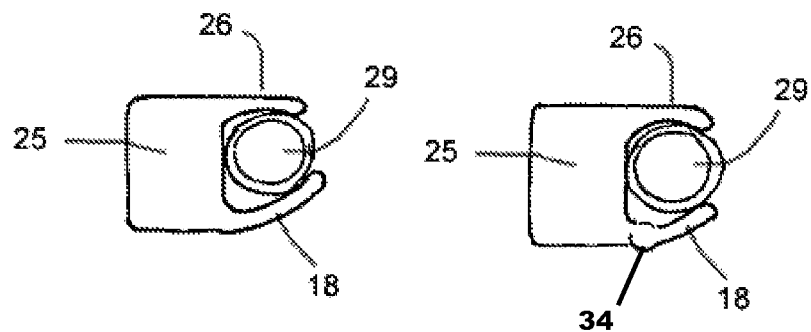
FIG. 4 is a cross-section through the distal superior tube guiding member of the insertion section of FIG. 2, while retaining a tube having an external diameter at the lower end of an operating range of endotracheal tube diameters.
FIG. 6 is a cross-section through the distal superior tube guiding member of an alternative insertion section, while retaining a tube having an external diameter at the lower end of an operating range of endotracheal tube diameters.
Figures 5, 7:
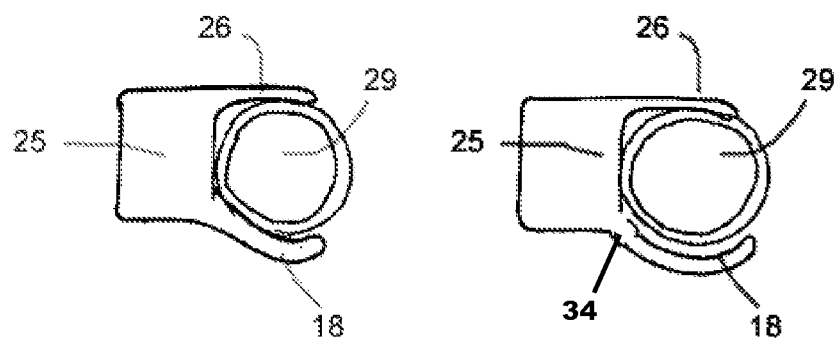
FIG. 5 is a cross-section through the distal superior tube guiding member of the insertion section of FIG. 2, while retaining a tube having an external diameter at the upper end of an operating range of endotracheal tube diameters.
FIG. 7 is a cross-section through the distal superior tube guiding member of an alternative insertion section, while retaining a tube having an external diameter at the upper end of an operating range of endotracheal tube diameters.

The distal superior tube guiding member is made from a resilient material, such as a resilient silicone or rubber-based material. FIG. 4 is a cross-section through the insertion section and distal superior tube guiding member while retaining a tube having an external diameter at the lower end of an operating range of external tube diameters. In the case of an insertion section for intubating adult humans, this may be around 8 mm. FIG. 6 is a cross-section through the insertion section and distal superior tube guiding member while retaining a tube having an external diameter at the upper end of an operating range of external tube diameters. In the case of an insertion section for intubating adult humans, this may be 12.3 mm.

As is apparent from FIGS. 4 and 6, the distal superior tube guiding member deforms laterally, away from the central axis of the insertion section when retaining a larger external diameter endotracheal tube. The overall breadth of the insertion section is greater when the larger external diameter endotracheal tube is retained than when the lower external diameter endotracheal tube is retained. As a result, the insertion section can reliably guide endotracheal tubes of a wide range of external diameters. If the distal superior tube guiding member was fixed in the position illustrated in FIG. 6, the small external diameter endotracheal tube would be loosely held and potentially extend from the distal end of the insertion section towards a patient's larynx at the wrong orientation during intubation.

Furthermore, although the breath of the insertion section can expand as required to guide a relatively large external diameter endotracheal tube, the overall thickness of the insertion section is less at the distal superior tube guiding member when retaining an endotracheal tube at the lower end of the operating range of endotracheal tube external diameters. Thus, the bulk of the insertion section is reduced when using small external diameter tubes, facilitating intubation and reducing the likelihood of a patient's teeth being damaged.

Instead of being formed entirely from a resilient material, the distal superior tube guiding member may comprise a portion formed from a rigid material and attached to the elongate support member by a resilient hinge 34. This embodiment is illustrated in FIGS. 6 and 8.

A plurality of tube guiding members may each be resilient (e.g. formed from a resilient material or comprising a rigid portion and a resilient hinge). Indeed, where multiple tube guiding member are provided, each tube guiding member may be resilient.

Figure 8:
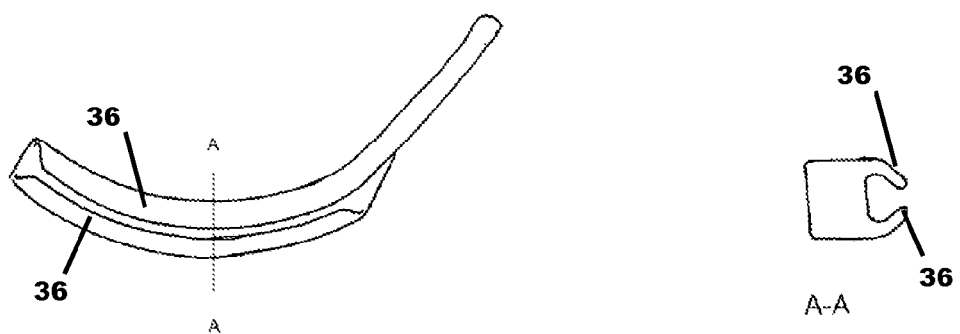
FIG. 8 is a side view of a laryngoscope insertion section having a lateral tube guide, without a retained endotracheal tube, and a cross-section through A-A.
Figure 9:
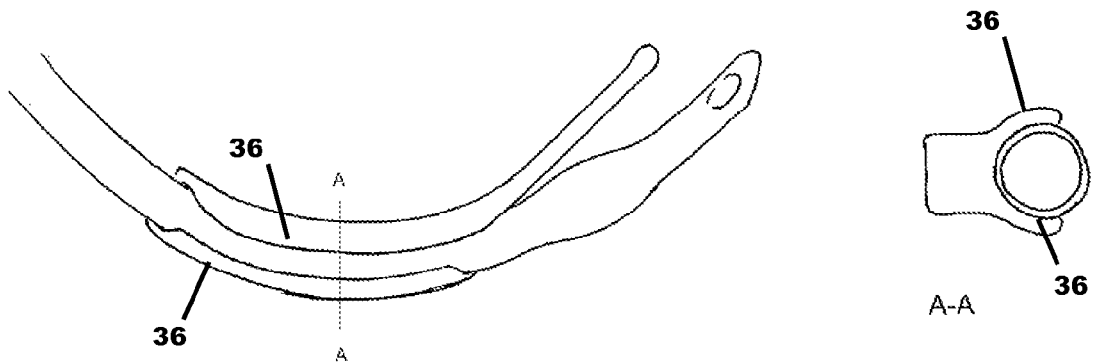
FIG. 9 is a side view of a laryngoscope insertion section having a lateral tube guide, without a retained endotracheal tube, and a cross-section through A-A.

A single resilient tube guiding member, or two opposed tube guiding members 36 may extend along some or all of the length of the insertion section, as illustrated in FIGS. 8 and 9. In this example, they extend from the most proximal location where the endotracheal tube contacts the tube guide to the most distal location where the endotracheal tube contacts the tube guide. Such resilient tube guiding members conform to the shape of a retained endotracheal tube.

Further variation and modifications may be considered by one skilled in the art, within the scope of the invention herein disclosed.

The invention claimed is:

1. A laryngoscope insertion section having a proximal end and a distal end for insertion into a patient's oral cavity, the insertion section comprising a tube guide for retaining an endotracheal tube and guiding a retained endotracheal tube towards a patient's larynx, the tube guide comprising a resilient tube guiding member biased towards a first position for retaining endotracheal tubes of a first external diameter and operable to a second position for retaining endotracheal tubes of a second external diameter, which second external diameter is at least 110% of the first external diameter, by the insertion of an endotracheal tube of the second external diameter.

2. A laryngoscope insertion section according to claim 1, wherein the tube guide comprises a central axis extending along the middle of the insertion section from the proximal end to the distal end of the insertion section, disregarding the tube guiding member, and the second position is further from the central axis than the first position.

3. A laryngoscope insertion section according to claim 1, wherein the thickness and/or breadth of the insertion section in a cross-section through the resilient tube guiding member is less when the resilient tube guiding member is in the first position than the second position.

4. A laryngoscope insertion section according to claim 1, wherein the insertion section comprises an elongate support member and the tube guide is located on a lateral side of the elongate support member.

5. A laryngoscope insertion section according to claim 4, wherein the overall breadth of the insertion section is greater at the location of resilient tube guiding member when the resilient tube guiding member is in the second position than in the first position.

6. A laryngoscope insertion section according to claim 1, wherein the resilient tube guiding member comprises or consists of resilient material.

7. A laryngoscope insertion section having a proximal end and a distal end for insertion into a patient's oral cavity, the insertion section comprising a tube guide for retaining an endotracheal tube and guiding a retained endotracheal tube towards a patient's larynx, wherein the thickness and/or the breadth of the tube guide is variable at at least one intraoral region located so as to be within a patient's oral cavity when the insertion section is fully inserted into a patient's oral cavity, to enable the overall thickness and/or breadth respectively of the insertion section at the intraoral region to vary depending on the external diameter of an endotracheal tube retained by the tube guide.

8. A laryngoscope insertion section according to claim 7, wherein the thickness and/or breadth of the insertion section, at the intraoral region, is larger when an endotracheal tube having the largest external diameter in an operating range of endotracheal tube sizes is retained by the tube guide than when an endotracheal tube having the lowest external diameter in an operating range of endotracheal tube sizes is retained by the tube guide.

9. A laryngoscope insertion section according to claim 7, wherein the insertion section further comprises an elongate support member and one or more tube guiding members extends from the elongate support member, wherein a said tube guiding member is resiliently mounted to the elongate support member at the intraoral region such as to vary the overall thickness or breadth of the insertion section dependent on the external diameter of a retained endotracheal tube.

10. A laryngoscope insertion section according to claim 8, wherein the or each said tube guiding member comprises or consists of resilient material.

11. A laryngoscope insertion section according to claim 7, wherein the insertion section comprises an elongate support member and wherein the tube guide is located on a lateral side of the elongate support member.

12. A laryngoscope insertion section according to claim 11, wherein the breadth of the insertion section depends on the external diameter of a retained endotracheal tube.

13. A laryngoscope having an insertion section retaining formation to demountably retain an insertion section according to claim 1.

14. A laryngoscope comprising a handle and an insertion section according to claim 1 fixedly attached thereto.

* * * * *